US012648925B2

(12) United States Patent
Lee

(10) Patent No.: US 12,648,925 B2
(45) Date of Patent: Jun. 9, 2026

(54) COMPOSITION FOR PREVENTING OR TREATING CANCER, CONTAINING MANASSANTIN A AND IMMUNE CHECKPOINT INHIBITOR OR EPITHELIAL GROWTH FACTOR RECEPTOR INHIBITOR

(71) Applicant: KYUNGPOOK NATIONAL UNIVERSITY INDUSTRY-ACADEMIC COOPERATION FOUNDATION, Daegu (KR)

(72) Inventor: You-Mie Lee, Gyeongsangbuk-do (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 1343 days.

(21) Appl. No.: 17/310,522

(22) PCT Filed: Feb. 6, 2020

(86) PCT No.: PCT/KR2020/001693

§ 371 (c)(1),
(2) Date: Aug. 6, 2021

(87) PCT Pub. No.: WO2020/162686

PCT Pub. Date: Aug. 13, 2020

(65) Prior Publication Data

US 2022/0117928 A1 Apr. 21, 2022

(30) Foreign Application Priority Data

Feb. 7, 2019 (KR) ........................ 10-2019-0014288
Feb. 7, 2019 (KR) ........................ 10-2019-0014289

(51) Int. Cl.

| | |
|---|---|
| ***A61K 39/395*** | (2006.01) |
| ***A61K 31/341*** | (2006.01) |
| ***A61K 31/517*** | (2006.01) |
| ***A61K 31/519*** | (2006.01) |
| ***A61K 31/5377*** | (2006.01) |
| ***A61K 31/675*** | (2006.01) |
| ***A61P 35/00*** | (2006.01) |
| *A61K 39/00* | (2006.01) |

(52) U.S. Cl.

CPC .......... *A61K 31/341* (2013.01); *A61K 31/517* (2013.01); *A61K 31/519* (2013.01); *A61K 31/5377* (2013.01); *A61K 31/675* (2013.01); *A61K 39/3955* (2013.01); *A61P 35/00* (2018.01); *A61K 2039/505* (2013.01)

(58) Field of Classification Search

None

See application file for complete search history.

(56) References Cited

U.S. PATENT DOCUMENTS

| | | | | |
|---|---|---|---|---|
| 8,946,289 B2 * | 2/2015 | Hong | ...................... | A61P 27/02 514/461 |
| 2019/0015507 A1 | 1/2019 | Xu et al. | | |

FOREIGN PATENT DOCUMENTS

| | | | | |
|---|---|---|---|---|
| KR | 10-2003-0019384 | A | | 3/2003 |
| KR | 10-2017-0013086 | A | | 2/2017 |
| WO | 2017/121318 | A1 | | 7/2017 |
| WO | WO/2017/121320 | | * | 7/2017 |

OTHER PUBLICATIONS

Choi et al., International Conference on 70th Anniversary of The Pharmaceutical Society of Korea, 2016, p. 165, p. 1-42 (Oral Presentation).

Lai et al. "LXY6090—a novel manassantin A derivative—limits breast cancer growth through hypoxia-inducible factor-1 Inhibition", OncoTargets and Therapy, 2016, vol. 9, pp. 3829-3840.

Lang et al. "A synthetic manassantin A derivative inhibits hypoxia-inducible factor 1 and tumor growth", PLOS One, 2014, vol. 9, Issue 6, e99584, 9 pages.

Semenza et al., "Evaluation of HIF-1 inhibitors as anticancer agents", Drug Discovery Today, 2007, vol. 12, Nos. 19/20, pp. 853-859.

* cited by examiner

*Primary Examiner* — Meera Natarajan

(74) *Attorney, Agent, or Firm* — Vorys, Sater, Seymour and Pease LLP; Mih Suhn Koh

(57) ABSTRACT

Provided is a method for preventing and/or treating cancer, the method including administering to a subject a composition containing manassantin and an immune checkpoint inhibitor, or manassantin A and an epithelial growth factor receptor inhibitor, as active ingredients. The composition of the presently claimed subject matter is expected to be effectively used to suppress, through co-administration, the proliferation, metastasis, relapse, or resistance to anticancer therapy of various solid cancers.

3 Claims, 3 Drawing Sheets

COMPOSITION FOR PREVENTING OR TREATING CANCER, CONTAINING MANASSANTIN A AND IMMUNE CHECKPOINT INHIBITOR OR EPITHELIAL GROWTH FACTOR RECEPTOR INHIBITOR

CROSS-REFERENCE TO RELATED APPLICATIONS

This application is a 371 of PCT/KR2020/001693 filed on Feb. 6, 2020, which claims the benefit of priority from Korean Patent Application No. 10-2019-0014288 filed on Feb. 7, 2019 and Korean Patent Application No. 10-2019-0014289 filed on Feb. 7, 2019, the contents of each of which are incorporated herein by reference in their entirety.

TECHNICAL FIELD

The present invention relates to a pharmaceutical composition for preventing or treating cancer, which includes manassantin A and an immune checkpoint inhibitor as active ingredients, and a pharmaceutical composition for preventing or treating cancer, which includes manassantin A and an epithelial growth factor receptor (EGFR) inhibitor as active ingredients.

BACKGROUND ART

Manassantin A is a type of lignan isolated from *Saururus chinensis* (Lour.) Baill, which is one of the medicinal plants, and has been found to have therapeutic effects on various diseases, for example, an effect of preventing or treating non-alcoholic fatty liver, an anti-inflammatory effect, an anti-human immunodeficient virus effect, an effect of improving a hyperpigmentation disease, and research on manassantin A is being actively conducted recently, but research on the correlation between manassantin A and cancer is still insufficient (Korean Patent 10-2017-0013086 A1).

Meanwhile, since advanced malignant tumor cells proliferate faster than endothelial cells forming blood vessels, newly-formed blood vessels are not normally distributed in cancer tissue, and therefore sufficient blood is not provided, and it is known that nutrient deficiency, acidification and oxygen deficiency are induced, and such a tumor microenvironment affects a cancer therapeutic effect. The median value of an oxygen partial pressure in normal tissue is substantially 40 to 60 mmHg, but in the case of solid cancer, the median value of an oxygen partial pressure is generally 10 mmHg or less. As cancer cells are adapted to such a hypoxic condition, they become more malignant under a hypoxic condition, and are known to have resistance to various cancer therapies such as chemotherapy and radiation therapy.

As a result of earnest research on the correlation between manassantin A and cancer, the present inventors confirmed that manassantin A exhibits an effect of preventing and/or treating cancer by alleviating the microenvironment in solid cancer and inhibiting the proliferation of cancer cells, and the therapeutic effect is considerably increased by co-administration of lung cancer therapeutics such as manassantin A and an immune checkpoint inhibitor, or manassantin A and an EGFR inhibitor. Thus, the present invention was completed.

DISCLOSURE

Technical Problem

To solve the above-described problems of the conventional art, the present invention is directed to providing a composition for preventing or treating cancer, which includes manassantin A an immune checkpoint inhibitor, or manassantin A and an epithelial growth factor receptor (EGFR) inhibitor as active ingredients, to alleviate a hypoxic condition in cancer tissue and inhibit the proliferation of cancer cells.

However, technical problems to be solved in the present invention are not limited to the above-described problems, and other problems which are not described herein will be fully understood by those of ordinary skill in the art from the following descriptions.

Technical Solution

The present invention provides a pharmaceutical composition for preventing or treating cancer, which includes manassantin A and an immune checkpoint inhibitor as active ingredients.

According to one embodiment of the present invention, the immune checkpoint inhibitor may be a programmed cell death protein 1 (PD-1) inhibitor, a programmed death-ligand 1 (PDL-1) inhibitor, a cytotoxic T-lymphocyte-associated antigen-4 (CTLA-4) inhibitor, a lymphocyte-activation gene 3 (LAG-3) inhibitor, a T-cell immunoglobulin and mucin-domain containing-3 (TIM-3) inhibitor, or a carcinoembryonic antigen-related cell adhesion molecule 1 (CEACAM1) inhibitor, but is not limited as long as it is an immune checkpoint inhibitor that can improve a therapeutic effect under a condition in which the microenvironment in solid cancer is alleviated by manassantin A.

According to another embodiment of the present invention, the manassantin A may exhibit an effect of treating cancer by inhibiting the expression of a hypoxia-inducible factor-1 alpha (HIF-1$\alpha$) protein in cancer cells.

According to still another embodiment of the present invention, the pharmaceutical composition is characterized by inhibiting cancer proliferation, metastasis and recurrence, or inhibiting resistance to an anticancer therapy, but is not limited as long as it is a part of the generally used methods of treating cancer.

According to yet another embodiment of the present invention, the cancer may be breast cancer, lung cancer, glioma, colorectal cancer, uterine cancer, ovarian cancer, prostate cancer, gastric cancer, brain cancer, multiple myeloma, childhood cancer, rectal cancer, colon cancer, thyroid cancer, oral cancer, pharyngeal cancer, laryngeal cancer, bladder cancer, kidney cancer, liver cancer, pancreatic cancer, bone cancer or skin cancer, but the cancer may be any type of solid cancer without limitation.

In addition, the present invention provides a pharmaceutical composition for preventing or treating cancer, which includes manassantin A and an EGFR inhibitor as active ingredients.

According to one embodiment of the present invention, the EGFR inhibitor may be any one or more selected from the group consisting of gefitinib, erlotinib, afatinib, brigatinib and icotinib, but is not limited as long as it is an EGFR inhibitor that is used as a lung cancer therapeutic.

According to another embodiment of the present invention, the manassantin A may exhibit a cancer therapeutic effect by inhibiting the expression of a HIF-1a protein in cancer cells.

According to still another embodiment of the present invention, the pharmaceutical composition may inhibit cancer proliferation, metastasis and recurrence, or inhibit resistance to an anticancer therapy, but is not limited as long as it is a part of the generally used methods of treating cancer.

According to yet another embodiment of the present invention, the cancer may be lung cancer, breast cancer, glioma, colorectal cancer, uterine cancer, ovarian cancer, prostate cancer, gastric cancer, brain cancer, multiple myeloma, childhood cancer, rectal cancer, colon cancer, thyroid cancer, oral cancer, pharyngeal cancer, laryngeal cancer, bladder cancer, kidney cancer, liver cancer, pancreatic cancer, bone cancer, or skin cancer, but the cancer may be any type of solid cancer without limitation.

In addition, the present invention provides a method of treating cancer, which includes administering the pharmaceutical composition into an individual.

In addition, the present invention provides a use of the pharmaceutical composition for treating cancer.

In addition, the present invention provides a use of the manassantin A and the immune checkpoint inhibitor, or the manassantin A and the EGFR inhibitor for producing a drug used for cancer.

Advantageous Effects

Since manassantin A according to the present invention can inhibit the expression of HIF-1α in solid cancer, and thus alleviate a microenvironment condition such as a hypoxic condition, and inhibit the proliferation of cancer cells, it is expected that manassantin A cannot only be used alone in prevention and/or treatment of solid cancer, but also be effectively used in treatment of various types of cancer because it can significantly improve its effect by co-administration with an anticancer therapeutic acting in a microenvironment of solid cancer, such as an epithelial growth factor receptor (EGFR) inhibitor such as gefitinib, or an immune checkpoint inhibitor.

MODES OF THE INVENTION

Figure 1:
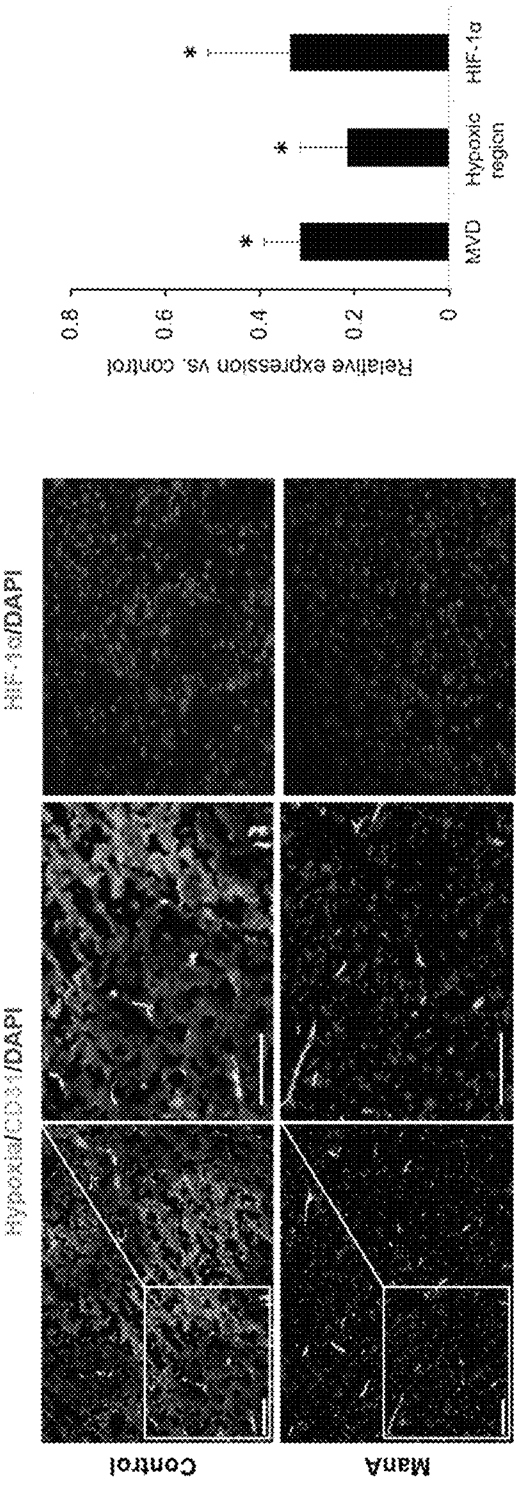
FIG. 1 shows results of confirming the effect of manassantin A according to one embodiment of the present invention on tumors.

The inventors confirmed that manassantin A alleviates the microenvironment conditions of solid cancer and inhibits the proliferation of cancer cells by effectively inhibiting HIF-1a expression, and thus can be used in cancer treatment, and the co-administration of the manassantin A with an immune checkpoint inhibitor or an epithelial growth factor receptor (EGFR) inhibitor can significantly improve a cancer therapeutic effect. Therefore, the present invention was completed.

The "manassantin A" used herein refers to a compound having the structure shown in Formula 1 below, and various biological activities of manassantin A, for example, an effect of treating a non-alcoholic liver disease, an anti-inflammatory disease, an anti-human immunodeficient virus effect, an effect of improving a hyperpigmentation disease, have been reported.

[Formula 1]

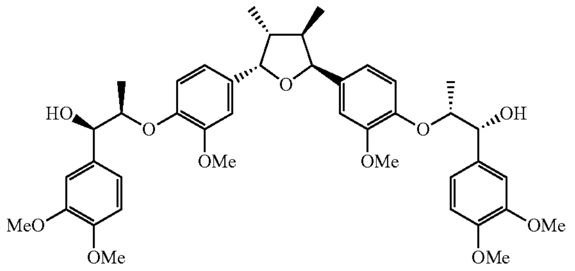

The "epidermal growth factor receptor (EGFR) inhibitor" used herein refers to an anticancer agent targeting the EGFR, and a type of anticancer agent that treats cancer by inhibiting a mechanism causing the proliferation of tumor cells through the activation of various intracellular mechanisms by binding of a transforming growth factor or a ligand to the EGFR, and is preferably gefitinib, erlotinib, afatinib, brigatinib or icotinib. However, the EGFR inhibitor is any material that can inhibit EGFR activation without limitation.

The "immune checkpoint inhibitor" used herein refers to a material that serves to restrain an immune checkpoint by activating T cells through direct binding in the microenvironment of solid cancer, and the immune checkpoint inhibitor is preferably a programmed cell death protein 1 (PD-1) inhibitor, a programmed death-ligand 1 (PDL-1) inhibitor, a cytotoxic T-lymphocyte-associated antigen-4 (CTLA-4) inhibitor, a lymphocyte-activation gene 3 (LAG-3) inhibitor, a T-cell immunoglobulin and mucin-domain containing-3 (TIM-3) inhibitor, or a carcinoembryonic antigen-related cell adhesion molecule 1 (CEACAM1) inhibitor, and may be in the form of an antibody. However, any material capable of inhibiting the expression and/or activity of a protein known as an immune checkpoint may be used without limitation.

The term "prevention" used herein refers to all actions of inhibiting a disease such as cancer or delaying the onset thereof by administration of a composition according to the present invention.

The term "treatment" used herein refers to all actions involved in alleviating or beneficially changing symptoms of cancer by administration of a composition according to the present invention.

The term "individual" refers to a subject to which a composition according to the present invention will be administered, but is not limited thereto.

The term "cancer" used herein is the generic term for all types of blood cancer and malignant solid tumors, which can expand locally by infiltration and systemically by metastasis. Specific examples of the cancer include, but are not particularly limited to, colorectal cancer, adrenal cancer, bone cancer, brain cancer, breast cancer, bronchial cancer, colon and/or rectal cancer, gallbladder cancer, gastrointestinal cancer, head and neck cancer, kidney cancer, laryngeal cancer, liver cancer, lung cancer, nervous tissue cancer, pancreatic cancer, prostate cancer, parathyroid cancer, skin cancer, gastric cancer, and thyroid cancer. Other examples of cancer include adenocarcinoma, adenoma, basal cell carcinoma, cervical dysplasia and in situ carcinoma, Ewing's sarcoma, epidermoid carcinomas, giant cell tumors, glioblastoma multiforma, hairy-cell tumor, intestinal ganglioneuroma, hyperplastic corneal nerve tumors, islet cell carcinoma, Kaposi's sarcoma, leiomyoma, leukemia, lymphoma, malignant carcinoid, malignant melanoma, malignant hypercalcemia, marfanoid habitus tumors, medullary carcinoma, metastatic skin carcinoma, mucosal neuroma, myelodisplastic syndrome, myeloma, mycosis fungoides, neuroblastoma, osteosarcoma, osteogenic and other sarcoma, ovarian tumors, pheochromocytoma, polycythermia vera, primary brain tumors, small-cell lung tumors, squamous cell carcinoma of both ulcerating and papillary types, seminoma, soft tissue sarcoma, retinoblastoma, rhabdomyosarcoma, renal cell tumors or renal cell carcinoma, veticulum cell sarcoma, and Wilm's tumors. It also includes astrocytoma, gastrointestinal stromal tumor (GIST), glioma or glioblastoma, renal cell carcinoma (RCC), hepatocellular carcinoma (HCC), pancreatic neuroendocrine cancer, and the like.

The "pharmaceutical composition" used herein may be a capsule, a tablet, a granule, an injectable, an ointment, a powder or a beverage, and the pharmaceutical composition may be applied to humans. The pharmaceutical composition may be, but is not limited to, formulated in the form of an oral formulation such as a powder, granules, a capsule, a tablet or an aqueous suspension, a preparation for external use, a suppository and a sterile injectable solution according to a conventional method. The pharmaceutical composition of the present invention may include a pharmaceutically acceptable carrier. As pharmaceutically acceptable carriers, a binder, a lubricant, a disintegrant, an excipient, a solubilizer, a dispersant, a stabilizer, a suspending agent, a coloring agent and a flavor may be used for oral administration, a mixture of a buffer, a preservative, a pain relief agent, a solubilizer, an isotonic agent and a stabilizer may be used for an injectable, and a base, an excipient, a lubricant and a preservative may be used for local administration. The pharmaceutical composition of the present invention may be prepared in various forms by being mixed with the above-described pharmaceutically acceptable carrier. For example, for oral administration, the pharmaceutical composition of the present invention may be prepared in various dosage forms such as a tablet, a troche, a capsule, an elixir, a suspension, a syrup and a wafer, and for injectables, the pharmaceutical composition of the present invention may be prepared in a unit dose ampoule or multiple dose forms. In addition, the pharmaceutical composition of the present invention may be formulated as a solution, a suspension, a tablet, a capsule or a sustained-release preparation.

Meanwhile, examples of carriers, excipients and diluents suitable for preparation may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. The examples of carriers, excipients and diluents may also include a filler, an anti-agglomerate, a glidant, a wetting agent, a fragrance, an emulsifier, and a preservative.

Administration routes for the pharmaceutical composition according to the present invention may include, but are not limited to, oral, intravenous, intramuscular, intraarterial, intramedullary, intrathecal, intracardiac, transdermal, subcutaneous, intraperitoneal, intranasal, enteral, local, sublingual or rectal administration. Oral or parenteral administration is preferable. The term "parenteral" used herein means subcutaneous, intradermal, intravenous, intramuscular, intraarticular, intrabursal, intrasternal, intrathecal, intralesional and intracranial injection techniques. The pharmaceutical composition of the present invention may be administered in the form of a suppository for rectal administration.rm A dose of the pharmaceutical composition of the present invention may vary according to various factors including the activity of a specific compound used, age, body weight, general health, sex, diet, administration time, administration route, excretion rate, drug formulation, and the severity of a specific disease to be prevented or treated, and a dosage of the pharmaceutical composition may be suitably selected by those of ordinary skill in the art depending on a patient's condition, body weight, the severity of a disease, a drug type, an administration route and an administration duration, and may be 0.0001 to 500 mg/kg or 0.001 to 500 mg/kg per day. The pharmaceutical composition of the present invention may be administered once a day or several times in divided portions. The dose does not limit the scope of the present invention in any way. The pharmaceutical composition according to the present invention may be formulated as a pill, a sugar-coated tablet, a capsule, a liquid, a gel, a syrup, a slurry or a suspension.

Hereinafter, to help in understanding the present invention, exemplary examples will be suggested. However, the following examples are merely provided to more easily understand the present invention, and not to limit the present invention.

EXAMPLES

Example 1: Confirmation of Anticancer Effect of Manassantin A

To confirm the effect of manassantin A on cancer, $4\times10^5$ cells of Lewis lung carcinoma (LLC), which is a mouse lung cancer cell line, were allografted into the subcutaneous route of the flank of a 6 to 7-week-old C57BL/6J mouse, thereby preparing a tumor animal model, and 2 mg/kg of manassantin A was treated through intraperitoneal injection on day 2, 4, 6, 8, or 10. As a control, the same amount of phosphate buffered saline (PBS) was injected. In addition, to measure a hypoxic state inside the tumor on day 17, 60 mg/kg of hypoxyprobe-1™ (pimonidazole hydrochloride; PIMO, HPI) was administered by intraperitoneal injection, and after 90 minutes, the mouse was sacrificed to extract the tumor. In addition, immunohistochemistry (HC) analyses were performed using the obtained tumor tissue. More particularly, the obtained tumor was fixed with 3.7% paraformaldehyde (PFA) and then dehydrated by treatment with a 10 to 40% sucrose solution step by step. In addition, after increasing the osmotic permeability of cells by treatment with 0.3% Triton X-100 and blocking with 5% bovine serum albumin (BSA), a rat anti-CD31 (BD Biosciences) or Alexa Fluor 647-conjugated anti-HIF-1 alpha antibody (Abcam) was treated and reacted at 4° C. for 16 hours. The mouse treated with the HIF-1 alpha antibody was a mouse which was not treated with hypoxyprobe-1™. In addition, unbound antibodies were washed with PBS, an Alexa Fluor 488-conjugated anti-rat IgG (Invitrogen) antibody, which is a secondary antibody, to which a fluorescent marker was bound, and a mouse anti-hypoxyprobe antibody (HPI) were treated, and reacted for 1 hour at room temperature. In addition, finally, a cell nucleus was stained with DAPI (Sigma-Aldrich) and observed using a confocal microscope, followed by quantifying a fluorescent value using ImageJ. All experiments were performed in triplicate, and then the results were verified by ANOVA to represent a significant difference between groups. P-values<0.05, which have statistical significance, were represented as means±standard deviations (SD). The results are shown in FIG. 1.

As shown in FIG. 1, it was confirmed that the hypoxic state generally observed in solid cancer was significantly reduced in an experimental group to which manassantin A was administered and the expression level of hypoxia-inducible factor-1 alpha (HIF-1a) was also significantly reduced. It was also confirmed that the microvessel density (MVD) of CD31-positive vascular endothelial cells was significantly reduced in the manassantin A-administered experimental group. From the above results, it was confirmed that manassantin A can inhibit the expression of HIF-1α known as a significant transcription factor associated with angiogenesis and anticancer agent resistance in solid cancer, and effectively inhibit the growth and metastasis of solid cancer.

Example 2: Confirmation of Effect of Co-Administration of Manassantin A and Gefitinib To confirm whether the co-administration of gefitinib, which is an EGFR inhibitor, and manassantin A exhibits an anticancer effect without side effects, a tumor animal model was prepared by the same method as in Example 1, and 5 mg/kg of manassantin A and 5 mg/kg of gefitinib were administered by intraperitoneal injection a total of five times once every three days. As a control, PBS was injected at the same dose as above. In addition, tumor growth and toxicity were observed every two days from day 8 when the tumor was first felt in the skin of the mouse. A width (mm), length (mm), and height (mm) of the tumor were measured using calipers and then multiplied to obtain a tumor volume ($mm^3$), and toxicity was confirmed by measuring the weight of the mouse. In addition, on day 17, the tumor was extracted, weighed and photographed. Animal breeding and all experimental procedures were conducted in accordance with the laws and regulations for animal tests. All experiments were performed in triplicate, and then the results were verified by ANOVA to represent a significant difference between groups. P-values<0.05, which have statistical significance, were represented as means±standard deviations (SD). The results are shown in FIG. 2.

Figure 2:
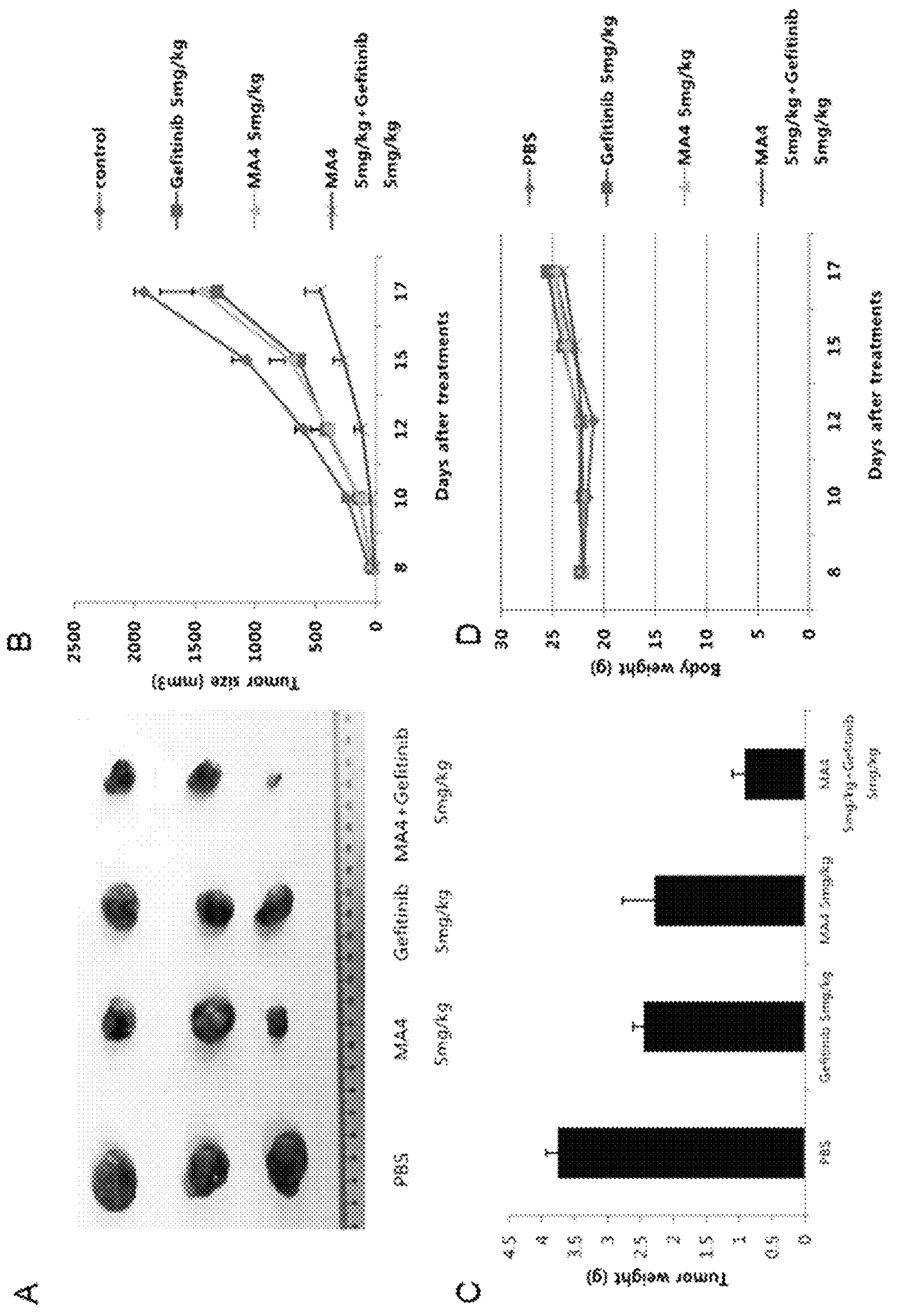
FIG. 2 shows results of confirming the effect of the co-administration of manassantin A according to one embodiment of the present invention and an epithelial growth factor receptor (EGFR) inhibitor on tumors.

As shown in FIG. 2, in the experimental group to which manassantin A and gefitinib were co-administered, compared to experimental groups to which each compound was administered alone, it was confirmed that a tumor size was significantly reduced, and there was no change in weight so that the co-administration exhibited low toxicity and a therapeutic effect increased 3-fold or more. From the above results, it was confirmed that a higher therapeutic effect could be exhibited with low side effects through the co-administration of manassantin A and gefitinib.

Example 3: Confirmation of Effect of Co-Administration of Manassantin a and Anti-PD-1 Antibody Recently, to confirm whether the co-administration of an anti-PD-1 antibody known as an immune checkpoint inhibitor and manassantin A exhibited an anticancer effect without side effects, a tumor animal model was prepared by the same method as in Example 1, and 2 mg/kg of manassantin A was administered by intraperitoneal injection on day 2, 4, 6, 8 and 10, and 15 mg/kg of the anti-PD-1 antibody was administered by intraperitoneal injection on day 3, 5, 7, 9 and 11. As a control, PBS was injected at the same amount as above. In addition, tumor growth and toxicity were observed every two days from day 8 when the tumor was first felt in the skin of the mouse. A width (mm), length (mm), and height (mm) of the tumor were measured using calipers and then multiplied to obtain a tumor volume ($mm^3$), and toxicity was confirmed by measuring the weight of the mouse. In addition, on day 17, the tumor was extracted, weighed and photographed. Animal breeding and all experimental procedures were conducted in accordance with the laws and regulations for animal tests. All experiments were performed in triplicate, and then the results were verified by ANOVA to represent a significant difference between groups. P-values<0.05, which have statistical significance, were represented as means±standard deviations (SD). The results are shown in FIG. 3.

Figure 3:
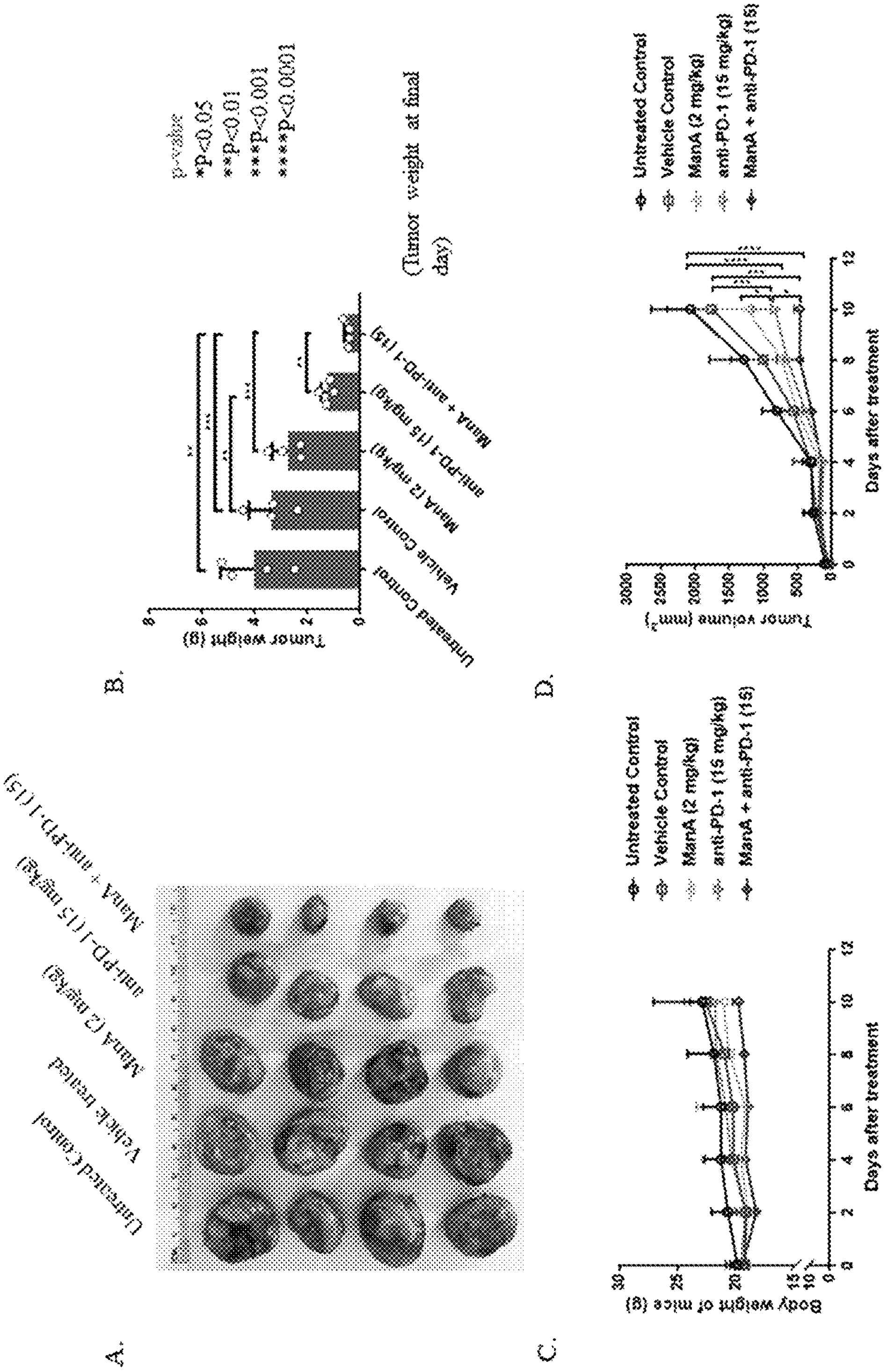
FIG. 3 shows results of confirming the effect of the co-administration of manassantin A according to one embodiment of the present invention and an immune checkpoint inhibitor on tumors.

As shown in FIG. 3, in an experimental group to which manassantin A and an anti-PD-1 antibody were co-administered, compared to experimental groups to which each compound was administered alone, it was confirmed that a tumor hardly grew. From the above results, it was confirmed that the co-administration of manassantin A and the anti-PD-1 antibody exhibited a high therapeutic effect with low side effects.

From the above results, it was confirmed that a composition according to the present invention, which includes manassantin A and an immune checkpoint inhibitor, or manassantin A and an EGFR inhibitor, can inhibit the expression of HIF-1α in solid cancer by manassantin A, thereby alleviating the microenvironmental condition such as a hypoxic condition, and inhibit an immune checkpoint by activating T cells in the microenvironment of solid cancer by the immune checkpoint inhibitor, such as an anti-DP-1 antibody, resulting in a considerably increased therapeutic effect in solid cancer. In addition, by increasing the therapeutic effect of the EGFR inhibitor such as gefitinib in solid cancer, it was confirmed that the therapeutic effect caused by co-administration can be significantly increased. Accordingly, it is expected that the composition of the present invention can be effectively used to inhibit the proliferation, metastasis or recurrence of solid cancer, or resistance to anticancer therapy.

It should be understood by those of ordinary skill in the art that the above descriptions of the present invention are exemplary, and the example embodiments disclosed herein can be easily modified into other specific forms without changing the technical spirit or essential features of the present invention. Therefore, it should be interpreted that the example embodiments described above are exemplary in all aspects, and are not limitative.

INDUSTRIAL APPLICABILITY

In the present invention, it was confirmed that a composition for preventing or treating cancer, which includes manassantin A and an immune checkpoint inhibitor, or manassantin A and an EGFR inhibitor as active ingredients can significantly increase a therapeutic effect through co-administration by increasing the effect of the inhibitor with manassantin A on solid cancer. Therefore, it is expected that the composition of the present invention can be effectively used to inhibit the proliferation, metastasis or recurrence of solid cancer, or resistance to anticancer therapy.

The invention claimed is:

1. A method for treating lung cancer, the method comprising: administering a pharmaceutically effective amount of a composition consisting of manassantin A and an anti-programmed cell death protein 1 (PD-1) antibody as active ingredients to a subject in need thereof.

2. The method of claim 1, wherein the manassantin A inhibits the expression of hypoxia-inducible factor-1 alpha (HIF-1α) protein in cancer cells.

3. The method of claim 1, which inhibits the proliferation, metastasis, recurrence of cancer, or resistance to anticancer therapy.

* * * * *